US012611260B2

(12) United States Patent
Govari

(10) Patent No.: US 12,611,260 B2
(45) Date of Patent: Apr. 28, 2026

(54) MULTI-ARM CATHETER WITH IMPROVED MAGNETIC LOCATION TRACKING

(71) Applicant: Biosense Webster (Israel) Ltd., Yokneam (IL)

(72) Inventor: Assaf Govari, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 562 days.

(21) Appl. No.: 17/890,600

(22) Filed: Aug. 18, 2022

(65) Prior Publication Data
US 2024/0058073 A1     Feb. 22, 2024

(51) Int. Cl.
| | |
|---|---|
| *A61B 34/20* | (2016.01) |
| *A61B 17/00* | (2006.01) |
| *A61B 18/00* | (2006.01) |
| *A61B 18/14* | (2006.01) |

(52) U.S. Cl.
CPC .......... *A61B 34/20* (2016.02); *A61B 18/1492* (2013.01); *A61B 2017/00725* (2013.01); *A61B 2018/0016* (2013.01); *A61B 2018/0022* (2013.01); *A61B 2018/00267* (2013.01); *A61B 2018/00357* (2013.01); *A61B 2018/00577* (2013.01); *A61B 2034/2053* (2016.02)

(58) Field of Classification Search
CPC ................ A61B 34/20; A61B 18/1492; A61B 2034/2053; A61B 2017/00725; A61B 2018/0016; A61B 2018/0022; A61B 2018/00267; A61B 2018/00357; A61B 2018/00577
See application file for complete search history.

(56) References Cited

U.S. PATENT DOCUMENTS

| | | | |
|---|---|---|---|
| 5,391,199 | A | 2/1995 | Ben-Haim |
| 6,239,724 | B1 | 5/2001 | Doron et al. |
| 6,332,089 | B1 | 12/2001 | Acker et al. |
| 6,484,118 | B1 | 11/2002 | Govari |

(Continued)

FOREIGN PATENT DOCUMENTS

WO          1996/05768 A1     2/1996

OTHER PUBLICATIONS

Extended European Search Report dated Jan. 23, 2024 for Application No. 23191840.0, 6 pages.

*Primary Examiner* — Linda C Dvorak
*Assistant Examiner* — Abigail Bock
(74) *Attorney, Agent, or Firm* — FBT Gibbons LLP

(57) ABSTRACT

A system includes a catheter and a processor. The catheter includes (i) a shaft for insertion into a cavity of an organ of a patient, (ii) an expandable distal-end assembly coupled to a distal end of the shaft and comprising splines fitted with spline-electrodes, (iii) a proximal position sensor and a respective proximate proximal electrode located both at a proximal end of the distal-end assembly, and (iv) an independent wire that extends at the distal tip, with a distal position sensor and a respective proximate distal electrode located both at a distal end of the independent wire. The processor is configured to estimate locations of one or more of the spline-electrodes by performing impedance measurements on the one or more of the electrodes, and to calibrate the impedance measurements based on signals received from the proximal position sensor and the distal position sensor and the respective proximal and distal electrodes.

18 Claims, 4 Drawing Sheets

(56) References Cited

U.S. PATENT DOCUMENTS

| | | | |
|---|---|---|---|
| 6,618,612 | B1 | 9/2003 | Acker et al. |
| 6,690,963 | B2 | 2/2004 | Ben-Haim et al. |
| 8,456,182 | B2 | 6/2013 | Bar-Tal et al. |
| 11,172,858 | B2 | 11/2021 | Olson et al. |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2014/0336494 | A1* | 11/2014 | Just ...................... A61B 5/6859 600/393 |
| 2017/0042449 | A1 | 2/2017 | Deno et al. |
| 2020/0206461 | A1 | 7/2020 | Govari et al. |
| 2021/0059608 | A1 | 3/2021 | Beeckler et al. |
| 2021/0113822 | A1 | 4/2021 | Beeckler et al. |
| 2022/0087736 | A1* | 3/2022 | Govari ............... A61B 18/1206 |
| 2022/0110675 | A1* | 4/2022 | Govari ............... A61B 18/1206 |
| 2022/0142713 | A1* | 5/2022 | Oren ...................... A61B 5/287 |

* cited by examiner

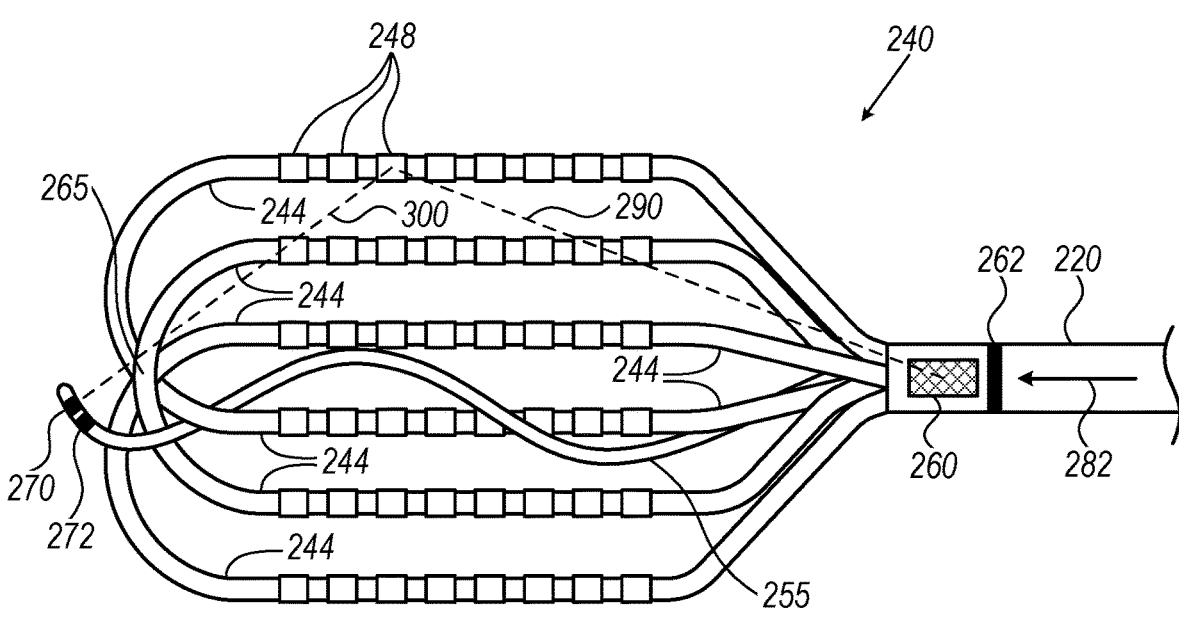

*FIG. 2*

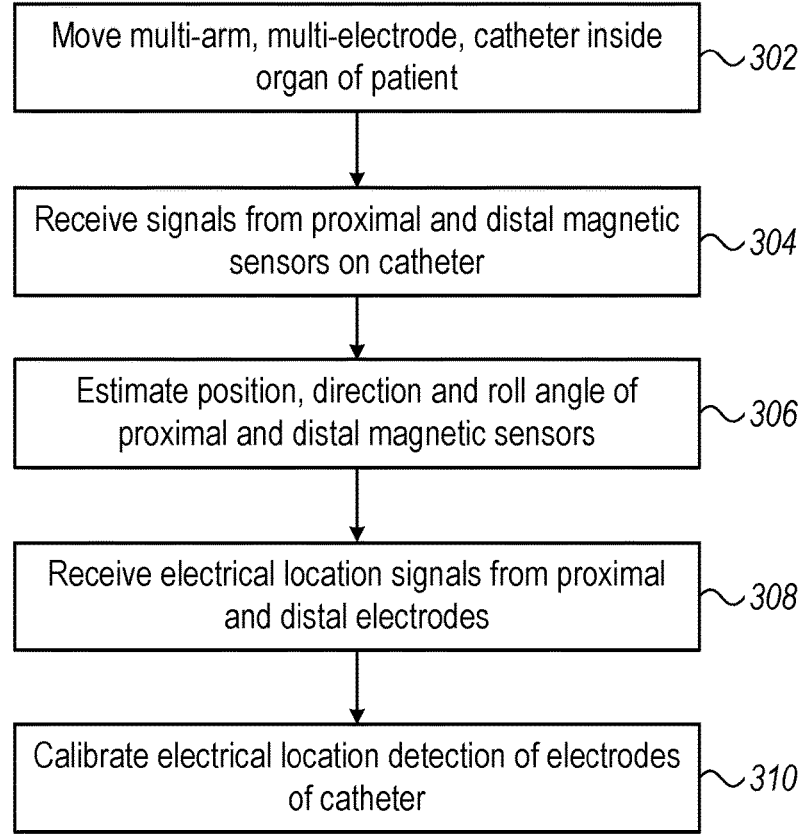

| Move multi-arm, multi-electrode, catheter inside organ of patient | 302 |

| Receive signals from proximal and distal magnetic sensors on catheter | 304 |

| Estimate position, direction and roll angle of proximal and distal magnetic sensors | 306 |

| Receive electrical location signals from proximal and distal electrodes | 308 |

| Calibrate electrical location detection of electrodes of catheter | 310 |

*FIG. 3*

MULTI-ARM CATHETER WITH IMPROVED MAGNETIC LOCATION TRACKING

FIELD OF THE DISCLOSURE

The present disclosure relates generally to invasive medical probes, and particularly to magnetic tracking of multi arm cardiac catheters.

BACKGROUND OF THE DISCLOSURE

Using magnetic sensors with multi-arm catheters was previously proposed in the patent literature. For example, U.S. Patent Application Publication 2020/0206461 describes a system that includes an expandable distal-end assembly, a proximal position sensor, a distal position sensor, and a processor. The expandable distal-end assembly is coupled to a distal end of a shaft for insertion into a cavity of an organ of a patient. The proximal and distal position sensors are located at a proximal end and a distal end of the distal-end assembly, respectively. The processor is configured to estimate a position and a longitudinal direction of the proximal sensor, and a position of the distal sensor, all in a coordinate system used by the processor. The processor is further configured to project the estimated position of the distal sensor on an axis defined by the estimated longitudinal direction, and calculate an elongation of the distal-end assembly by calculating a distance between the estimated position of the proximal sensor and the projected position of the distal sensor.

As another example, 2021/0059608 describes a system that includes a catheter including an insertion tube and a first position sensor, a pusher including a second position sensor, and an expandable assembly including flexible strips disposed circumferentially around a distal portion of the pusher, with first ends of the strips connected to the distal end of the insertion tube and second ends of the strips connected to the distal portion of the pusher, the flexible strips bowing radially outward when the pusher is retracted, processing circuitry to receive a respective position signal from the first and second position sensors, compute location and orientation coordinates for the position sensors subject to a constraint that the position sensors are coaxial and have a same orientation, compute a distance between the computed location coordinates of the position sensors, and find position coordinates of the flexible strips responsively to at least the computed distance.

The present disclosure will be more fully understood from the following detailed description of the examples thereof, taken together with the drawings in which:

BRIEF DESCRIPTION OF THE DRAWINGS

FIG. 2 is a schematic side view of a flat multi-electrode catheter fitted with a distal magnetic sensor, in accordance with an example of the present disclosure;

FIG. 3 is a flow chart that schematically illustrates a method and algorithm for calibrating electrical location detection using proximal and distal magnetic sensors, in accordance with an example of the present disclosure;

DETAILED DESCRIPTION OF EXAMPLES

Overview

Figure 1:
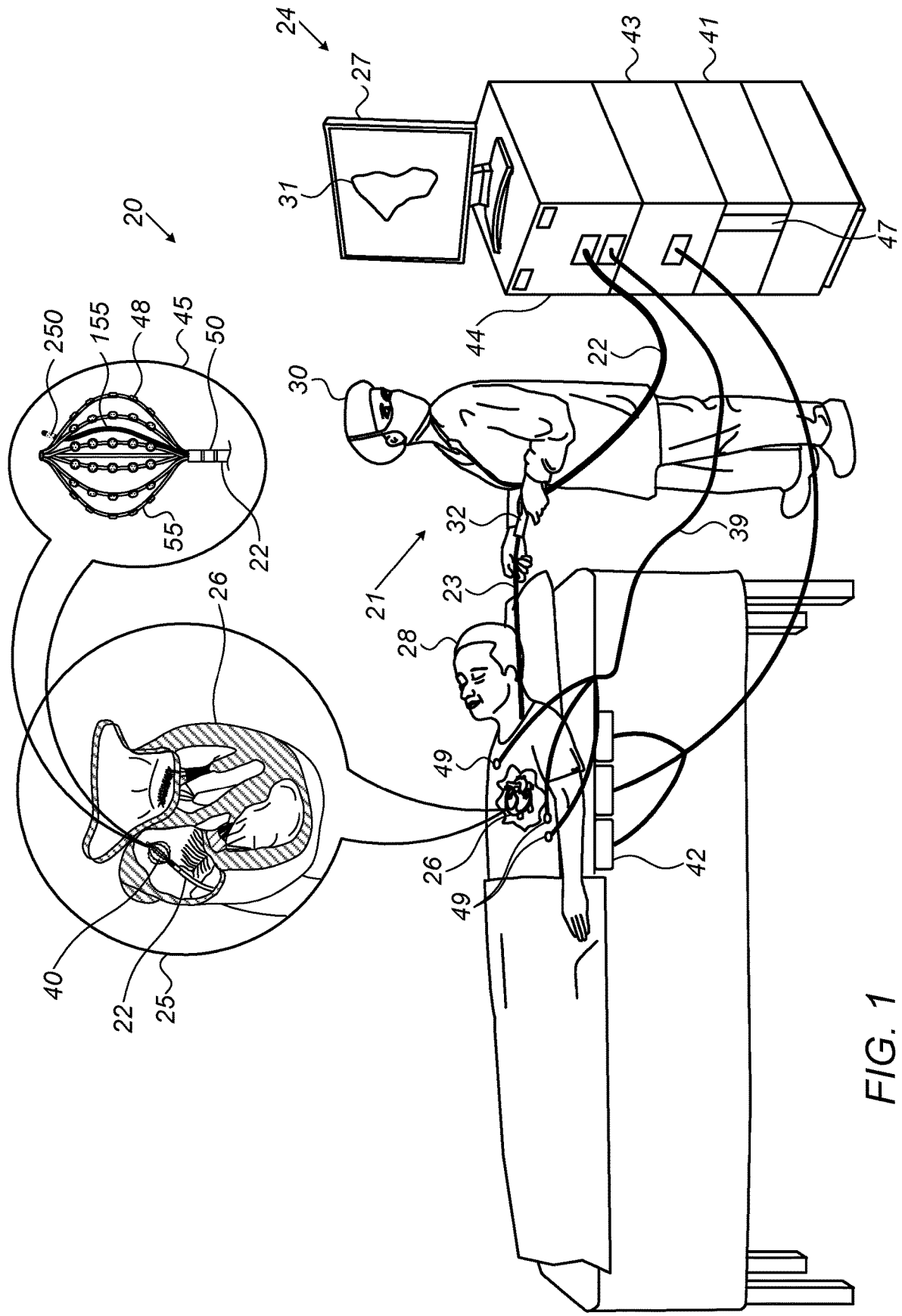
FIG. 1 is a schematic, pictorial illustration of a system for electro-anatomical mapping comprising a basket catheter, in accordance with an example of the present disclosure.

An expandable distal-end assembly of a catheter for insertion into a cavity of an organ of a patient, such as a basket catheter, may be employed in various clinical applications, such as electro-anatomical mapping and ablation of the cavity walls, e.g., cardiac chamber walls. To this end, an expandable distal-end assembly typically carries multiple electrodes fitted on flexible splines of an expandable distal-end assembly, the electrodes named hereinafter "spline-electrodes." The position, direction, roll-angle and shape of the distal-end assembly (collectively named hereinafter "location") can be estimated using an electrical tracking system. Such a system tracks the expandable distal-end assembly using, for example, impedance signals generated by the multiple spline-electrodes.

However, the electrical tracking technique may not produce a sufficiently accurate location of the expandable distal-end assembly inside an organ of a patient.

Examples of the present disclosure that are described herein provide a technique to calibrate the electrical location detection using readings from proximal and distal magnetic sensors, and respective proximal and distal electrode, each pair of magnetic sensor and electrode fitted proximally and distally to the distal-end assembly, respectively.

Typically, the proximal magnetic sensor, e.g., a TAS (triaxial sensor), is mounted on a distal end of the shaft of the catheter, with a proximal electrode mounted on the shaft in close proximity to the magnetic sensor (e.g., up to several millimeters proximally to the magnetic sensor), as shown in FIG. 2 below. The proximal sensor provides accurate 3D positioning for the shaft and has a stable and pre-known (e.g., sufficiently rigid) geometrical relationship with the proximal electrode and the electrodes on the splines. The proximal magnetic sensor can be used for anatomical mapping of the heart chamber, and also for calibrating impedance-based location measurements performed using the electrodes on the splines. To calibrate electrical detection, a processor compares the output of the proximal electrode to the proximal magnetic sensor Based on this comparison, the processor estimates the location of each of the electrodes on the splines based on their own output. The impedance-based location detection may be used to detect a location of each of the electrodes, for example for electro-anatomical mapping.

However, since the proximal magnetic sensor is located on the shaft of the catheter (at or near the proximal end of the aforementioned assembly), the electrodes on the splines precede the proximal sensor in the movement direction (i.e., the TAS reaches an anatomical location being diagnosed last) which impairs and delays the anatomical mapping, as well as the calibrated impedance location detection.

To overcome the limitation of using a proximal pair of magnetic and electrical sensors for calibration, some examples of the disclosed technique utilize the flexible splines that form the catheter tip so they include an additional spline or independent wire that extends from the distal end of the shaft past the distal tip of the distal-end assembly. The wire may optionally be more compliant than the splines of the distal-end assembly, and may be made from different materials, such as metallic ones or plastics. The independent wire extends distally from the distal tip formed by the splines. This independent wire includes an additional magnetic sensor referred to as a distal sensor, and an additional electrode in proximity to the distal magnetic sensor, to additionally provide magnetic-based position sensing at the most distal point of the catheter that may be used to improve the accuracy in the calibration of the electrical detection. The distal sensor may comprise, for example, a TAS, SAS (single axis magnetic sensor) or DAS (dual axis magnetic sensor). Optionally, calibration of position sensing with the spline electrodes may be based on the distal magnetic position sensing.

In some examples, using magnetic position signals obtained from the proximal sensor and from the distal sensor, the processor compares the electrodes output to the magnetic sensor output at two locations (proximal and distal). Based on these two comparisons, the processor can now estimate more accurately from electrical detection, the location of each of the electrodes on the splines, i.e., based on their own output. As the electrode assembly geometry is fixed relative to the proximal sensor, this calculation enables the processor to calculate locations of the electrodes relative to the distal sensor location by using the proximal magnetic sensor as an intermediate step. In other words, the proximal sensor enables the tracking system to track the electrode locations relative to the distal sensor location, even though the location of the distal sensor relative to the electrodes is not fully known by itself due to the flexible nature of the additional spline.

The independent wire (e.g., additional spline) is sufficiently flexible (e.g., more flexible and less stiff) than the electrode-carrying splines with electrodes, and is designed so that it does not interfere with the catheter tip mechanics (e.g., does not add stiffness to the catheter tip). In one example, the independent wire loosely weaves through the electrode-carrying splines. In another example, the independent wire extends in a direction generally parallel to the splines. The independent wire and the splines including the electrodes may be formed from different materials and/or may have different dimensions.

In another example, the independent wire can be advanced before the splines with electrodes are advanced off the sheath.

While the disclosure discusses magnetic sensors as providing location-indicative signals that are accurate enough to calibrate an electrical location detection, other types of sensors that are also sufficiently accurate, may be used instead.

System Description

FIG. 1 is a schematic, pictorial illustration of an electro-anatomical mapping system 20, in accordance with an example of the present disclosure. A physician 30 navigates a catheter 21 comprising a basket assembly 40 (made by Biosense-Webster), or, alternatively, a flat catheter (shown in FIG. 2), seen in detail in inset 45, to a target location in a heart 26 of a patient 28, by manipulating shaft 22, using a manipulator 32 near the proximal end of the catheter, and/or deflection from a sheath 23. In the example seen in inset 25, physician 30 uses catheter 21 to perform electro-anatomical mapping of a cardiac chamber.

Basket assembly 40 is inserted in a folded configuration, through sheath 23, and only after basket assembly 40 exits sheath 23 does basket assembly 40 regain its intended functional shape. By containing basket assembly 40 in a folded configuration, sheath 23 also serves to minimize vascular trauma on its way to the target location.

Basket assembly 40 further comprises multiple expandable spines 55, which may be mechanically flexible, all of which are coupled to multiple electrodes 48. Electrodes 48 may be used as sensing electrodes and as ablation electrodes. Magnetic sensors 50 and 250, and electrodes 48, are connected by wires running through shaft 22 to various driver circuitries in a console 24.

Processor 41 receives electrical impedance signals that are measured between electrodes 48 and surface electrodes 49. A method for tracking the locations of electrodes 48 using the measured impedances is implemented in various medical applications, for example in the CARTO™ system, produced by Biosense-Webster (Irvine, California) and is described in detail in U.S. Pat. No. 8,456,182, which is assigned to the assignee of the current disclosure. This method is sometimes called Advanced Catheter Location (ACL).

Basket assembly 40 incorporates a proximal magnetic sensor 50, seen in inset 45, at the distal edge of shaft 22 (i.e., at the proximal edge of basket assembly 40). Typically, although not necessarily, sensor 50 is a triaxial sensor (TAS). A second magnetic sensor 250 is fitted on a distal end of an additional weaving spline 155 included in the basket catheter. Sensor 250 may be a single axis sensor (SAS) or a triaxial sensor (TAS), for example.

As seen, system 20 comprises a magnetic-sensing subsystem to estimate locations of sensors 50 and 250 inside a cardiac chamber of heart 26. Patient 28 is placed in a magnetic field generated by a pad containing magnetic field generator coils 42, which are driven by unit 43. The magnetic fields generated by coils 42 generate signals in sensors 50 and 250, which are indicative of position and/or direction and/or roll angle. The generated signals are transmitted to console 24 and become corresponding electrical inputs to a processor 41. The processor uses the signals, which are stored in a memory 47, to calibrate the aforementioned electrical location detection (e.g., ACL detection).

The method of location sensing using external magnetic fields and magnetic sensors, such as sensors 50 and 250, is implemented in various medical applications, for example, in the CARTO™ system, produced by Biosense-Webster, which is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1.

Processor 41, typically a general-purpose computer, is further connected, via suitable front end and interface circuits 44, to receive signals from surface electrodes 49. Processor 41 is connected to surface electrodes 49 by wires running through a cable 39 to the chest of patient 28.

In an example, processor 41 additionally receives various spatial and electrophysiological signals via an electrical interface 44, and uses the information contained in these signals to construct an electro-anatomical map 31 of the cavity. During and/or following the procedure, processor 41 may display electro-anatomical map 31 on a display 27.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables processor 41 to perform the disclosed steps, as described below.

The example illustration shown in FIG. 1 is chosen purely for the sake of conceptual clarity. Additional types of catheters can be equipped with the disclosed solution for a distal location sensor, such as the aforementioned flat catheter comprising a planar array of high-density mapping electrodes, the catheter described in U.S. Pat. No. 11,172, 858 assigned to the assignee of the present disclosure. Furthermore, the disclosed solution for incorporating a distal location sensor can be adapted, mutatis mutandis, to a balloon catheter.

Multi-Arm Flat Catheter with Improved Magnetic Location Tracking

FIG. 2 is a schematic side view of a flat multi-electrode catheter fitted with a distal magnetic sensor 270, in accordance with an example of the present disclosure. The flat catheter may comprise a high-density array of spline-electrodes 248. This array of spline-electrodes 248 is coupled to an expandable distal-end assembly 240 of arms 244 (e.g., splines 244) which extend in a plane that is substantially parallel with a longitudinal axis 282 of catheter shaft 220. Optionally, each of the arms is precisely separated laterally from each other to facilitate exact spacing between spline-electrodes 248 on adjacent arms. The arms may be coupled to one another at a distal tip 265 with a bushing sleeve (not shown) is fitted on the distal edge of shaft 220 to reduce vibrations of the splines.

Based on signals from a proximal magnetic sensor 260 and a respective proximal electrode 262, located at a distal end of shaft 220, processor 41 estimates at least a longitudinal direction (i.e., a direction which is parallel to longitudinal axis 282 defined by the distal end of shaft 22). At the same time, processor 41 estimates a location of distal sensor 270 and respective distal electrode 272 that is fitted just distally to expandable distal-end assembly 240 at a distal end of a wire 255.

As seen, independent wire 255 loosely weaves through the splines 244 with spline-electrodes 248 and extends past the distal end 265 or near the distal end. The independent wire may be loosely connected to distal tip 265 (e.g., with a connector that allows the independent wire to advance and retract while being held). The independent wire 255 extends distally from distal tip 265 formed by splines 244. Since magnetic-based sensor 270 and respective electrode 272 are located at a distal end of independent wire 255, just distally to distal tip 265, they provide magnetic-based position sensing and respective electrical position signal at the most distal point of the catheter.

Using the coordinate system of the magnetic tracking system, processor 41 is able to calculate the coordinate of each spline-electrode 248 in the coordinate system of the tracking system (e.g., by calculating the triangle side 290 based on known geometry, or previous calibration, and lastly calculating triangle side 300. Triangle side 300 gives the location of a spline-electrode 248 relative to the distal sensor 270 location. Note that, since independent wire 255 is not rigid, the measurements of signals from distal sensor 270, proximal sensor 260, respective electrodes 262 and 272 and electrodes 248 should be acquired within a sufficiently short time interval.

Independent wire 255 is sufficiently flexible (e.g., more flexible and less stiff than splines 244) and is designed so that it does not interfere with the catheter tip mechanics (e.g., does not add stiffness to the catheter tip).

Method of Calibrating Electrical Location Detection of Multi-Arm Catheter Using Improved Magnetic Location Tracking FIG. 3 is a flow chart that schematically illustrates a method and algorithm for calibrating electrical location detection using proximal and distal magnetic sensors, in accordance with an example of the present disclosure. The algorithm, according to the presented example, carries out a process that begins with physician 30 moving basket assembly 40, or flat catheter 240, which is equipped with proximal and distal magnetic sensors, such as sensors 50 and 250, or sensors 260 and 270, respectively, inside an organ of a patient (e.g., inside a cardiac cavity).

In an example, as basket assembly 40 moves within the cardiac cavity, processor 41 receives signals from sensors 50 and 250, at a signal receiving step 304. Based on the signals received from proximal and distal sensors, processor 41 estimates position, direction, and roll angle of the sensors, at sensor location estimations step 306.

At an electrode detecting signal step 308, the processor receives electrical location signals (e.g., impedances) from proximal and distal electrodes 262 and 272 (seen in FIG. 2).

Finally, using the estimated position, direction, and roll angle of the sensors, the processor calibrates electrical location signals from respective electrodes 262 and 272, and using and the known geometric relationship between the proximal and distal electrodes and the spline-electrodes, the processor calibrates an electric location detection that uses electrical signals acquired by the electrodes of the catheter, at a calibration step 310.

The example flow chart shown in FIG. 3 is chosen purely for the sake of conceptual clarity. The flow chart shown in FIG. 3 is applicable, with the necessary changes being made, to any expandable distal-end assembly of a catheter for insertion into a cavity of an organ of a patient, such as a balloon catheter. The present example may also comprise additional steps of the algorithm, such as calibrating the electrical location system to estimate a change in shape of the catheter based not only on magnetic signals, but also on contact force sensors and known mechanical properties of the flexible distal-end assembly.

Basket and Balloon Catheters with Improved Magnetic Location Tracking

Figure 4:
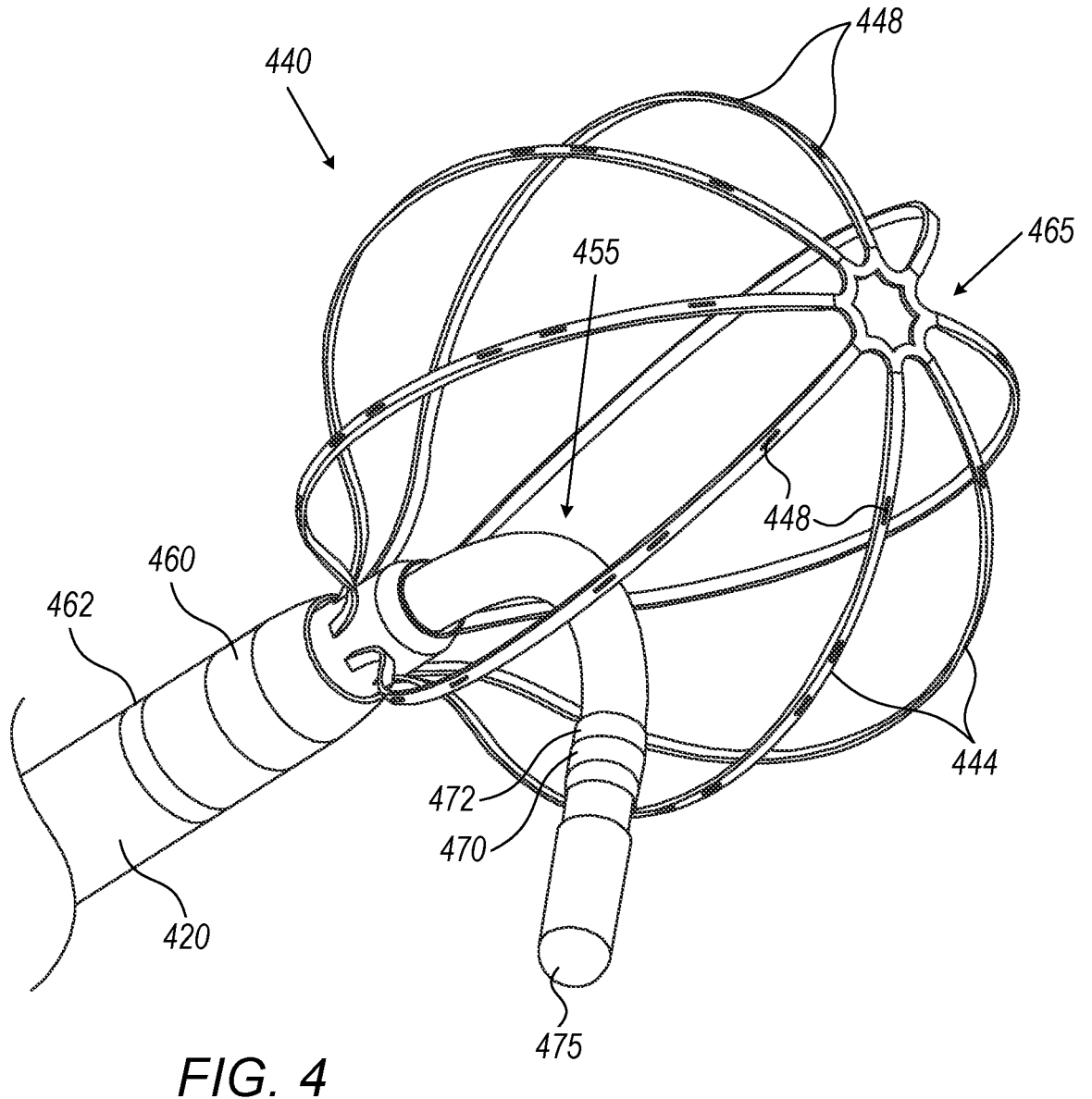
FIG. 4 is a schematic orthographic view of a basket multi-electrode catheter assembly fitted with a distal magnetic sensor, in accordance with an example of the present disclosure.

FIG. 4 is a schematic orthographic view of a basket multi-electrode catheter assembly 440 fitted with a distal magnetic sensor 470, in accordance with an example of the present disclosure. Basket assembly 440 is coupled to a distal end of a shaft 420. The basket comprises a high-density array of spline-electrodes 448 disposed on splines 444. The splines are mechanically coupled to one another at a distal tip 465.

Based on signals from a proximal magnetic sensor 460 and a respective proximal electrode 462, located at a distal end of shaft 420, processor 41 estimates at least a longitudinal direction defined by the distal end of shaft 420. At the same time, processor 41 estimates a location of distal sensor 470 and respective distal electrode 472 that are fitted on a distal end of an independent wire 455.

As seen, independent wire 455 loosely extends past some of splines 448, letting magnetic-based sensor 470 and respective electrode 472 to be located in vicinity of some of electrodes 448. This way, sensor 470 and electrode 472 provide magnetic-based position sensing and respective electrical position signal at a further distal portion of the catheter (e.g., with respect to sensor 460 and electrode 462).

Using the coordinate system of the magnetic tracking system, processor 41 is able to calculate the coordinate of some of spline-electrode 448 in the coordinate system of the tracking system. Using known geometry of the basket assembly, processor 41 can provide more accurate locations of rest of electrode 448 than otherwise achieved.

Note that, since independent wire 455 is not rigid, the measurements of signals from distal sensor 470, proximal sensor 460, respective electrodes 462 and 472 and electrodes 448 should be acquired within a sufficiently short time interval.

Finally, independent wire 455 may comprise an ablation electrode tip 475 to perform RF ablations as necessary.

Figure 5:
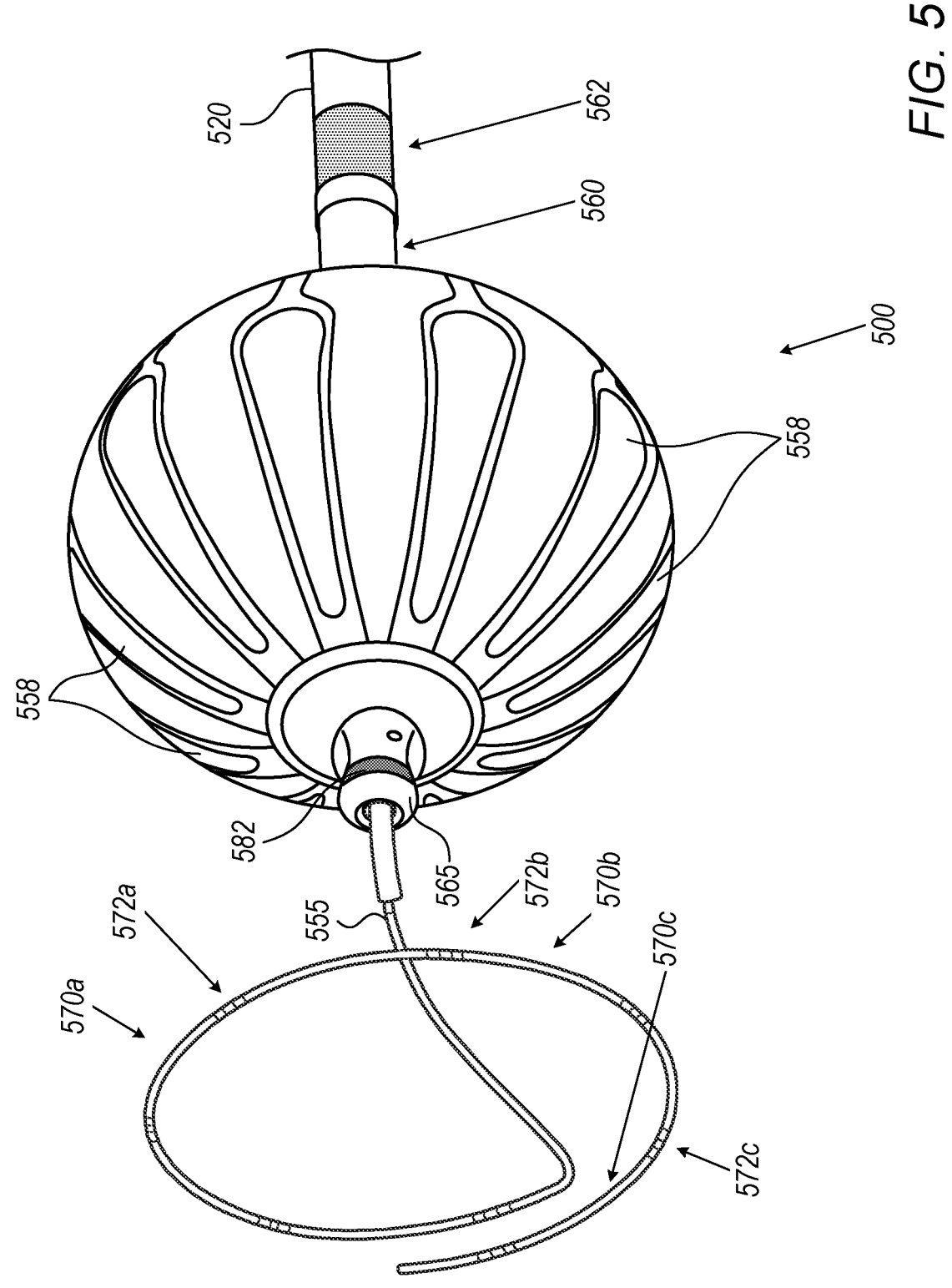
FIG. 5 is a schematic perspective view of a balloon multi-electrode catheter assembly fitted with distal magnetic sensors, in accordance with an example of the present disclosure.

FIG. 5 is a schematic perspective view of a balloon multi-electrode catheter assembly 500 fitted with distal magnetic sensors (570a, 570b, and 570c), in accordance with an example of the present disclosure. The magnetic sensors are disposed on an independent wire 555, and are oriented at 120 degrees relative to each other. Each magnetic sensor can be associated with a respective electrode of electrodes (572a, 572b, and 572c).

Balloon assembly 500 is coupled to a distal end of a shaft 520. The balloon is disposed with an array of electrodes 558 A distal electrode 582 is disposed on a distal tip of balloon assembly 500.

As seen, independent wire 555 extends distally of the balloon, letting magnetic-based sensors (570a, 570b, and 570c) and respective electrodes (572a, 572b, and 572c) to be located distally to electrodes 558. This way, they provide magnetic-based position sensing and respective electrical position signal at the most distal point of the balloon catheter.

EXAMPLES

Example 1

A system (20) includes a catheter (21) and a processor (41). The catheter includes (i) a shaft (220) for insertion into a cavity of an organ (26) of a patient (28), (ii) an expandable distal-end assembly (240) coupled to a distal end of the shaft, the distal-end assembly comprising splines (244) fitted with spline-electrodes (248), (iii) a proximal position sensor (260) located at a proximal end of the distal-end assembly, and a respective proximal electrode (262) located at the proximal end of the distal-end assembly, in proximity of the proximal position sensor, and (iv) an independent wire (255) that extends at a distal tip (265), a distal position sensor (270) located at a distal end of the independent wire, and a respective distal electrode (272) located at the distal end of the independent wire, in proximity of the distal position sensor. The processor is configured to estimate locations of one or more of the spline-electrodes (248) by performing impedance measurements on the one or more of the electrodes, and to calibrate the impedance measurements based on signals received from the proximal position sensor (260) and the distal position sensor (270) and the respective proximal and distal electrodes (262, 272).

Example 2

The system according to example 1, wherein the processor (41) is configured to calibrate the impedance measurements by measuring a location of the distal position sensor (270) and using the measured location to calibrate a location of the distal electrode (272), and measuring a location of the proximal position sensor (260) and using the measured location to calibrate a location of the proximal electrode (262).

Example 3

The system according to any of examples 1 and 2, wherein the proximal position sensor (260) and the distal position sensor (270) are magnetic sensors (50, 250).

Example 4

The system according to any of examples 1 through 3, wherein the distal position sensor (270) is located on a portion of the independent wire (255) that extends distally from the distal-end assembly (240).

Example 5

The system according to any of examples 1 through 4, wherein the independent wire (255) is mechanically more flexible than the splines (244) of the expandable distal-end assembly (240).

Example 6

The system according to any of examples 1 through 5, wherein the independent wire (255) is loosely connected to the distal tip (265).

Example 7

The system according to any of examples 1 through 6, wherein the expandable distal-end assembly (240) comprises a flat array.

Example 8

The system according to any of examples 1 through 6, wherein the expandable distal-end assembly (240) comprises a basket.

Example 9

The system according to any of examples 1 through 6, wherein the expandable distal-end assembly (240) comprises a balloon.

Example 10

A method includes inserting into a cavity of an organ of a patient a shaft (220) of a catheter (21), the catheter further comprising (i) an expandable distal-end assembly (240) coupled to a distal end of the shaft, the distal-end assembly comprising splines (244) fitted with spline-electrodes (248), (ii) a proximal position sensor (260) located at a proximal end of the distal-end assembly, and a respective proximal electrode (262) located at the proximal end of the distal-end assembly, in proximity of the proximal position sensor, and (iii) an independent wire (255) that extends at a distal tip (265), a distal position sensor (270) located at a distal end of the independent wire, and a respective distal electrode (272) located at the distal end of the independent wire, in proximity of the distal position sensor. Locations of one or more of the spline-electrodes (248) are estimated by performing impedance measurements on the one or more of the electrodes, and calibrating the impedance measurements based on signals received from the proximal position sensor (260) and the distal position sensor (270) and the respective proximal and distal electrodes (262, 272).

Although the examples described herein mainly address cardiac applications, the methods and systems described herein can also be used in other medical applications in which a catheter is inserted into a cavity of an organ of a patient, such as with a navigable Ear, Nose, & Throat (ENT) probe.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a catheter, comprising:
   a shaft for insertion into a cavity of an organ of a patient;
   an expandable distal-end assembly coupled to a distal end of the shaft, the distal-end assembly comprising a plurality of splines fitted with spline-electrodes, each of the plurality of splines being coupled to at least one other of the plurality of splines at their distal ends;
   a proximal position sensor located at a proximal end of the distal-end assembly, and a respective proximal electrode located at the proximal end of the distal-end assembly in proximity of the proximal position sensor; and
   an independent wire that is extendable and retractable from the distal end of the shaft and terminates in a free distal end, the independent wire being extendable and retractable independent of the plurality of splines of the distal-end assembly, a distal position sensor located at the distal end of the independent wire, and a respective distal electrode located at the distal end of the independent wire in proximity of the distal position sensor; and
   a processor configured to estimate locations of one or more of the spline-electrodes by performing impedance measurements on the one or more of the spline-electrodes, and to calibrate the impedance measurements based on signals received from the proximal position sensor and the distal position sensor and the respective proximal and distal electrodes.

2. The system according to claim 1, wherein the processor is configured to calibrate the impedance measurements by measuring a location of the distal position sensor and using the measured location of the distal position sensor to calibrate a location of the distal electrode, and measuring a location of the proximal position sensor and using the measured location of the proximal position sensor to calibrate a location of the proximal electrode.

3. The system according to claim 1, wherein the proximal position sensor and the distal position sensor are magnetic sensors.

4. The system according to claim 1, wherein the distal position sensor is located on a portion of the independent wire that extends distally from the distal-end assembly.

5. The system according to claim 1, wherein the independent wire is mechanically more flexible than the splines of the expandable distal-end assembly.

6. The system according to claim 1, wherein the independent wire is loosely connected to the distal end of the distal-end assembly such that the independent wire remains extendable and retractable while loosely connected to the distal end of the distal-end assembly.

7. The system according to claim 1, wherein the expandable distal-end assembly comprises a flat array.

8. The system according to claim 1, wherein the expandable distal-end assembly comprises a basket.

9. The system according to claim 1, wherein the expandable distal-end assembly comprises a balloon.

10. A method, comprising:
inserting into a cavity of an organ of a patient a shaft of a catheter, the catheter comprising:
   an expandable distal-end assembly coupled to a distal end of the shaft, the distal-end assembly comprising a plurality of splines fitted with spline-electrodes, each of the plurality of splines being coupled to at least one other of the plurality of splines at their distal ends;
   a proximal position sensor located at a proximal end of the distal-end assembly, and a respective proximal electrode located at the proximal end of the distal-end assembly in proximity of the proximal position sensor; and
   an independent wire that is extendable and retractable from the distal end of the shaft and terminates in a free distal end, the independent wire being extendable and retractable independent of the plurality of splines of the distal-end assembly, a distal position sensor located at a distal end of the independent wire, and a respective distal electrode located at the distal end of the independent wire in proximity of the distal position sensor; and
estimating locations of one or more of the spline-electrodes by performing impedance measurements on the one or more of the spline-electrodes, and calibrating the impedance measurements based on signals received from the proximal position sensor and the distal position sensor and the respective proximal and distal electrodes.

11. The method according to claim 10, wherein calibrating the impedance measurements comprises measuring a location of the distal position sensor and using the measured location of the distal position sensor to calibrate a location of the distal electrode, and measuring a location of the proximal position sensor and using the measured location of the proximal position sensor to calibrate a location of the proximal electrode.

12. The method according to claim 10, wherein the proximal position sensor and the distal position sensor are magnetic sensors.

13. The method according to claim 10, wherein the distal position sensor is located on a portion of the independent wire that extends distally from the distal-end assembly.

14. The method according to claim 10, wherein the independent wire is mechanically more flexible than the splines of the expandable distal-end assembly.

15. The method according to claim 10, wherein the independent wire is loosely connected to the distal end of the distal-end assembly such that the independent wire remains extendable and retractable while loosely connected to the distal end of the distal-end assembly.

16. The method according to claim 10, wherein the expandable distal-end assembly comprises a flat array.

17. The method according to claim 10, wherein the expandable distal-end assembly comprises a basket.

18. The method according to claim 10, wherein the expandable distal-end assembly comprises a balloon.

* * * * *